(12) United States Patent
Badilini

(10) Patent No.: US 8,560,054 B2
(45) Date of Patent: Oct. 15, 2013

(54) METHOD AND APPARATUS FOR EXTRACTING OPTIMUM HOLTER ECG READING

(75) Inventor: Fabio F. Badilini, Breschia (IT)

(73) Assignee: A.M.P.S., LLC, New York, NY (US)

( * ) Notice: Subject to any disclaimer, the term of this patent is extended or adjusted under 35 U.S.C. 154(b) by 420 days.

(21) Appl. No.: 11/745,744

(22) Filed: May 8, 2007

(65) Prior Publication Data

US 2007/0265538 A1 Nov. 15, 2007

Related U.S. Application Data

(60) Provisional application No. 60/798,523, filed on May 8, 2006.

(51) Int. Cl.
*A61B 5/04* (2006.01)

(52) U.S. Cl.
USPC .......................................... 600/509

(58) Field of Classification Search
USPC ............ 600/500, 509, 515, 523, 485, 517; 607/4, 5, 9
See application file for complete search history.

(56) References Cited

U.S. PATENT DOCUMENTS

| | | | |
|---|---|---|---|
| 4,583,553 A | 4/1986 | Shah et al. | |
| 5,058,597 A | 10/1991 | Onoda et al. | |
| 5,343,870 A | 9/1994 | Gallant et al. | |
| 6,609,023 B1 * | 8/2003 | Fischell et al. | 600/515 |
| 6,643,548 B1 * | 11/2003 | Mai et al. | 607/17 |
| 6,701,184 B2 | 3/2004 | Henkin | |
| 6,811,536 B2 * | 11/2004 | Sun et al. | 600/500 |
| 7,123,953 B2 * | 10/2006 | Starobin et al. | 600/516 |
| 7,142,924 B2 | 11/2006 | Legay et al. | |
| 2003/0208129 A1 * | 11/2003 | Beker et al. | 600/509 |
| 2004/0186388 A1 | 9/2004 | Gerasimov | |

OTHER PUBLICATIONS

European Search Report of Corresponding EP application (Appl. No. 07 762 005.2) total 6 pages, dated.
International Search Report from corresponding PCT application (PCT/US07/68462 filed May 8, 2007 (total 5 pages).

* cited by examiner

*Primary Examiner* — Carl H Layno
*Assistant Examiner* — Paula J Stice
(74) *Attorney, Agent, or Firm* — Christensen O'Connor Johnson Kindness PLLC

(57) ABSTRACT

The present invention is for a method and apparatus for extracting optimum ECG data from within a optimum timeperiod. The method and apparatus require setting a timeperiod in which to extract ECG data, setting thresholds for noise, determining a segment with stable heart rate, and to measure the ECG data of the time period. Once the parameters are set and the data is collected, optimum data according to the parameters set by the user are extracted for use and analysis, such that the ECGs that are free from noise and have a stable heart rate are retrieved from the desired timeperiod window. The invention can be used in a software program, may be programmable into a Holter monitors, or as well as applicability in other related monitoring devices.

15 Claims, 12 Drawing Sheets

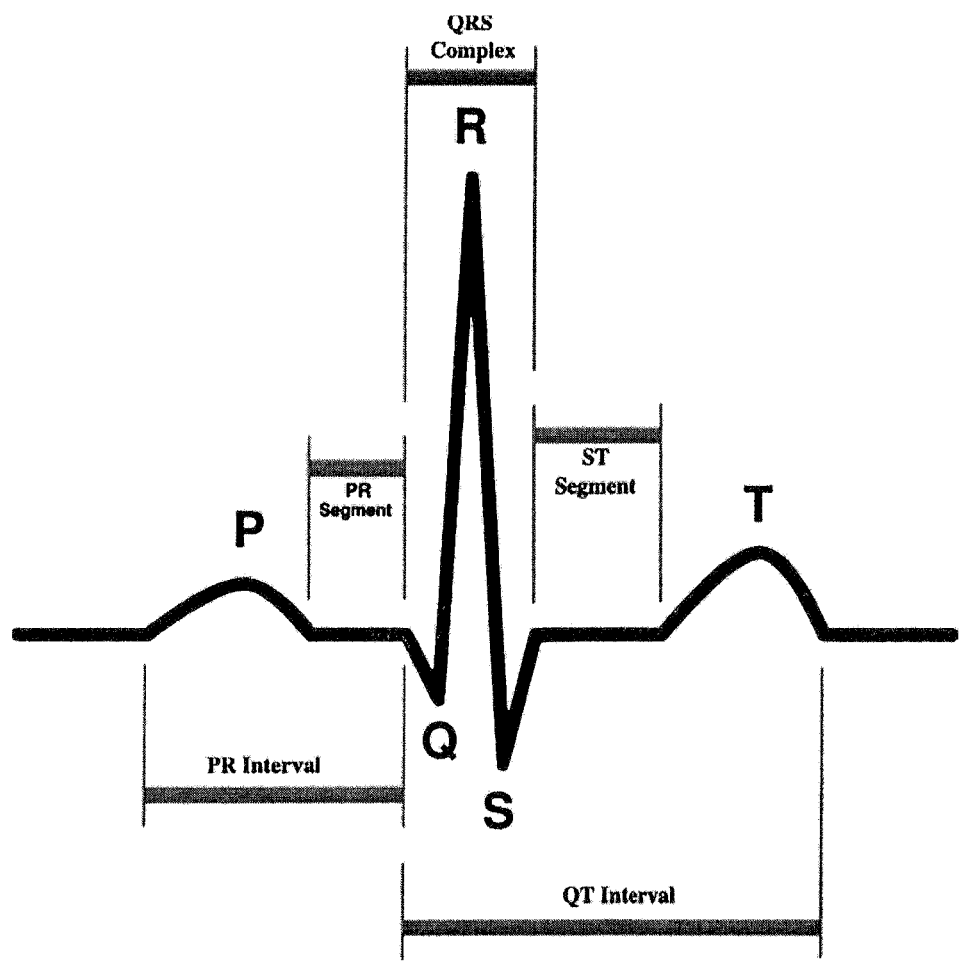

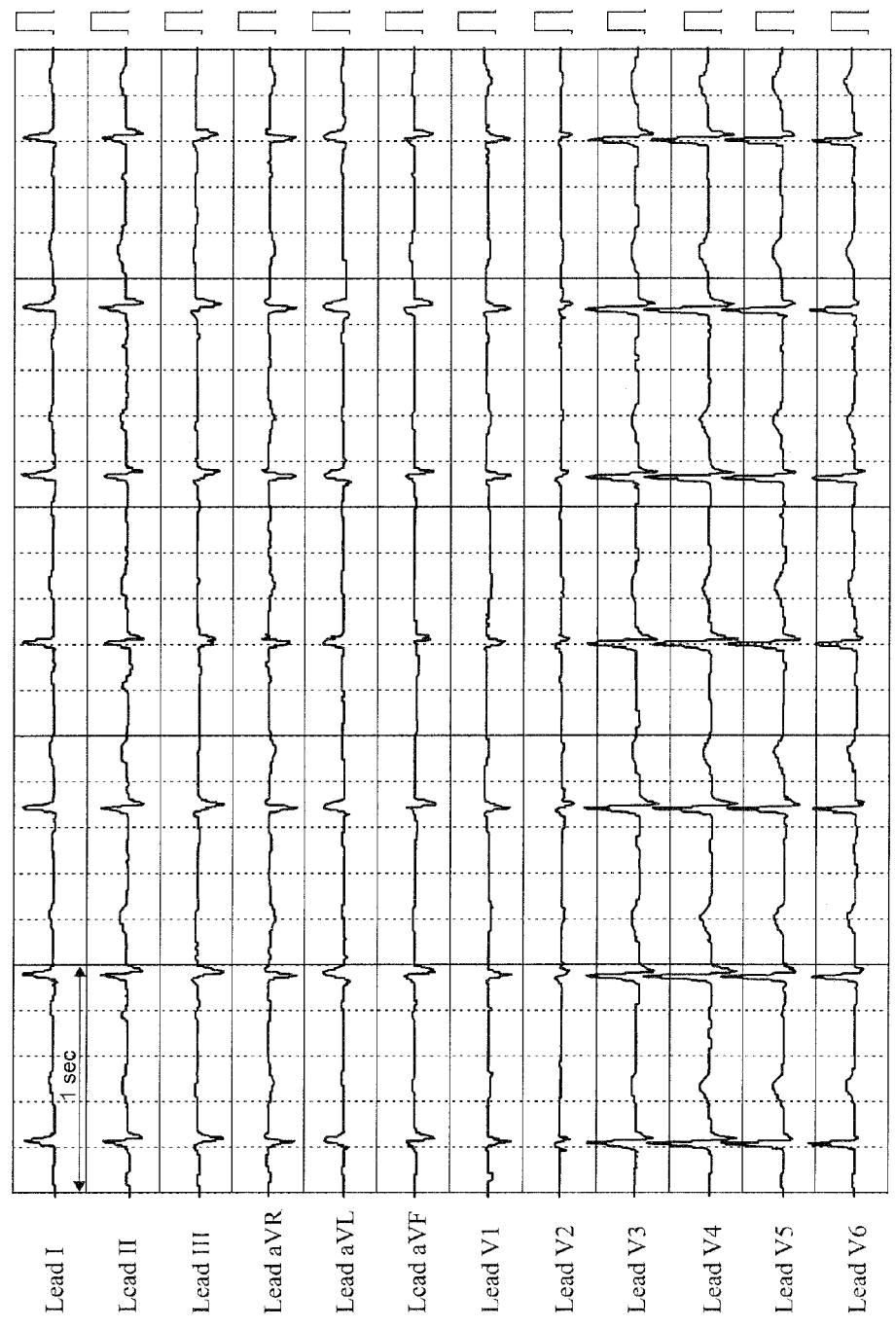

Fig. 4

RR = 672
QT = 350
QTcb = 427
QTcf = 400

RR = 850
QT = 382
QTcb = 414
QTcf = 403

METHOD AND APPARATUS FOR EXTRACTING OPTIMUM HOLTER ECG READING

CROSS-REFERENCE TO RELATED APPLICATIONS

This application claims priority from U.S. Provisional Patent Application Ser. No. 60/798,523, filed May 8, 2006.

FIELD OF THE INVENTION

This invention relates to medical monitoring devices and methods of analyzing data. Specifically, the invention relates to a method and apparatus for collecting and extracting optimum electrocardiography data from ECG recording devices such as Holter monitors.

BACKGROUND OF THE INVENTION

Electrocardiograms (ECGs) are graphic depictions of electrical activity in the heart. ECGs are produced by electrocardiographs which are available as stand alone devices, portable devices, and are also integrated into various types of vital signs recording and monitoring devices. ECGs are depicted by time (ms) versus voltage (μV) and typically are represented by five or six points as a waveform. The typical five data points on an ECG, as shown in FIG. 1A, are the P wave, QRS complex (represented as the combination of the Q, R, and S waves respectively), and T wave. The less frequently seen sixth point is a U wave. The data produced from the graphical depictions are useful in diagnosis of patients to determine what, if any, and the extent to which heart-related problems exist in a patient. For instance, ECGs are used in diagnosing: cardiac arrhythmias (irregular heart rhythms), myocardial infarction (heart attacks), hyper- and hypokalemia (high or low potassium levels, respectively), blockage, ischemia (loss of oxygen due to lack of blood flow possibly from blockage), and may also assist in diagnosis of non-heart related ailments. Accordingly, ECGs are known and proven to be valuable tools in diagnosis heart and even non-heart-related problems with patients.

Particularly, the ECG waveforms are useful in determining whether certain conditions exist or the predisposition of such conditions occurring based on established patterns. As shown in FIG. 1A, ECGs are defined by several characteristics in the PQRST waveform. Particularly, important information can be derived by measuring the time between certain waveforms; commonly reviewed time intervals are those between the P wave and the beginning of the QRS interval (known as the PR interval) and the time between the QRS complex and the T wave (known as the QT interval), which are shown in FIG. 1A. Further, as shown in FIG. 1A, there are other relevant data from the PR segment, the QRS complex, and the ST segment.

Typically, ECGs are used as diagnostic tools in various settings such as hospitals and doctors offices. ECGs taken in such instances are generally limited in scope, to the time of minutes, and therefore may not always provide sufficient information for diagnosis or data for analysis. Accordingly, there are known in the art portable devices used for recording ECGs and other patient data for extended periods of time where required to assist in diagnosis, monitoring, or other analysis measures.

Portable electrocardiography devices are known devices in the art for use in recording ECGs on ambulatory patients. These devices are also known as Holter monitors. The devices have significance in the medical industry as they can record ECGs for longer periods of time, such as minutes, hours, or days, and also in intervals of the same sort, as prescribed by a physician, without restricting the patient to doctor's offices or a hospital bed. The purpose of having prolonged measurements of such devices is useful to assist in diagnosing whether heart conditions are present in a patient, and upon individual review of the actual data, what types of conditions may exist. Further, such devices can assist simply for monitoring the heart in situations where the patient may be at risk for certain conditions, which can be identified from patterns displayed on the ECG, but which may also not be readily apparent from the few minutes of data typically gathered in a doctor's office.

Because of their physical size, portable devices used to have less robust technical specifications (i.e. limited number of recorded channels, lower sampling rates, and smaller voltage resolution). However, most recent models are now matching the technical specification of standard resting ECG machines. Currently, several commercial companies offer today high resolution Holter monitors with 12-lead storage at 1000 Hz sampling rate with a few microvolts resolution (e.g. H12+ recorder from Mortara Instruments, the CM3000 recorder from Getemed-GE, or the Spiderview recorder from ELAMedical).

As mentioned above, Holter monitors can be used for monitoring patients for various purposes. One such purpose can be monitoring patients undergoing clinical trials for various procedures or drug testing, specifically in FDA clinical trials for approval of devices and drugs onto the market. Emerging FDA and global regulatory guidelines require all new drug candidates to undergo more rigorous Phase I QT studies conducted by a centralized laboratory using validated, digital analysis of ECG waveforms and manual QT interval determinations by designated cardiologists; this type of study is commonly referred to as the Thorough QT study or TQT study. As an example, electrocardiography data is continuously recorded up to 72 hours to monitor ischemia, ventricular and supra-ventricular dysrhythmias, conduction abnormalities, QT interval, and heart rate variability.

Further, certain clinical studies require that ECGs be taken when the concentration of a drug in a patient's circulatory system is at a predetermined level. It is often important to take the ECG when the level of drug is at its maximum to determine the possibility of certain conditions on the heart by such experimental drugs.

Phase I studies may last as long as two weeks. During that time test subjects wear Holter monitors which record ECG data while letting the subject remain ambulatory. This is often a requirement since test subjects do not wish to remain in bed for the duration of a Phase I trial.

While portable devices are known in the art for ambulatory patients, there are several issues that arise during the use of these devices. For instance, while data is recorded, the signal can either receive interference or pick up "noise" which is reflected on the ECG. Another important factor that needs to be accounted for in ambulatory patients, particularly for QT studies, is that the ECG measurements should be taken when the heart rate is stable. In other words, the ECG measurements should be relatively consistent or has minimal or no variation from one ECG measurement to the next. Indeed, many parameters such as the QT interval need some time, generally a few minutes, to reach a steady state after occurrence of a heart rate variation, such as heart rate acceleration or deceleration. This phenomenon is known in the literature and it is commonly referred to as the hysteresis heart rate effect. Ideally relevant measurements should thus be taken in a clean and hysteresis-free segment of the ECG signal.

As mentioned above, problems related to noise, interference, varied heart rates are known. In the case of Holter monitors, the patient is moving with 12-leads attached to his or her body. Such motion can and does generate noise in the sensed ECG signals. In addition, ECG signals are not reliable when the patient's heart is accelerating or decelerating. Other issues can result as such devices are susceptible to electromagnetic interference from power lines and other environmental factors. Thus, prior art devices and methods do not account for these dynamic condition which interfere with reliable readings.

Therefore, a method of extracting data free from noise and from segments of stable heart rates from recorded ECG data, collected from Holter and similar monitors, is desired.

Further, an apparatus that can utilize a method for collecting optimum ECG data is desired.

SUMMARY OF THE INVENTION

The invention comprises, in one form thereof, a method comprising the steps of: providing electrocardiography data; determining segments with stable heart rate on said data; providing a noise threshold; and extracting an electrocardiography data point from said electrocardiography data outside said noise threshold and having said stable or average heart rate.

The invention comprises, in another form thereof an apparatus for extracting optimum electrocardiography data comprising: an ECG recording device; and a software program capable of: determining a segment with a stable heart rate; defining a noise threshold; and extracting an electrocardiography data points wherein said data points are outside said defined noise threshold and have said stable heart rate.

An advantage of the present invention is that the it allows the user (or an independent and completely automated process), especially in the clinical drug testing field, to shift through hours of ECG data to identify the necessary best extractions within set time periods or throughout the recorded ECG data record.

A further advantage of the present invention is that the invention allows for automated instructions while ECG recording devices such as Holter monitors are worn.

As previously mentioned, in clinical drug testing periods, monitors must be worn to assess the affect of drugs on the heart. Accordingly, certain data must be collected and analyzed at periods throughout the day and at expected time periods, such as times of maximum drug interaction or absorption into the circulatory system. Therefore, necessarily, the clinician will want information free from other environmental or other irrelevant factors (i.e. noise or heart rate changes) so that such factors do not affect the data analysis; either with respect to the affects of drugs or even devices on the patient itself or, specifically, the heart. Accordingly, the present invention greatly increases the ability of the clinician to quickly and effectively eliminate data having such environmental factors in set time periods.

The invention overcomes the disadvantages of the prior art by providing a program for running a Holter apparatus to provide a window of readings that are free from noise and unstable heart rates. The invention provides one or more reading windows before and after the expected time of drug level maximum in the blood stream. During the windows the invention extracts the best ECGs for each timeout point. The best ECGs are the ones with the lowest noise following a stable hear rate. One or more extractions may be made. In the preferred embodiment, the extractions do not overlap and a single abnormal beat will eliminate a potential extraction.

BRIEF DESCRIPTION OF THE DRAWINGS

The present invention is disclosed with reference to the accompanying drawings, wherein:

FIG. 1A is an exemplary electrocardiogram depicting and labeling the waveform;

FIG. 1B is an exemplary 12-lead electrocardiogram;

FIG. 4 is an example of dialog boxes from a software program embodying the method of the present invention;

FIGS. 6A and 6B are differentiated by less than two minutes where FIG. 6A depicts an ECG following a sudden heart rate change and FIG. 6B is preceded by a stable heart rate;

The examples set out herein illustrate an embodiment of the invention but should not be construed as limiting the scope of the invention in any manner.

DETAILED DESCRIPTION

The present invention includes a method, which may be embodied in a software program, for running a Holter monitor to provide one or multiple data points that are free from noise and that are preceded by a stable heart rate (i.e. removal of hysteresis heart rate), thereby eliminating outside or environmental factors which could interfere with the data analysis performed on the ECGs. Referring to FIG. 1A, there is shown an ECG figure depicting an exemplary ECG waveform, and FIG. 1B shows an exemplary ECG from a 12-lead device. The ECG are recordings from Holter monitors that record data taken from leads attached to patient being monitored. Current ECG Holter monitors, while useful for recording of the ECG itself, do not permit the selection of extractions distinguishing between the ECGs where noise and unstable heart rates occur. Conversely, the present invention provides a method for automatic data extraction of optimum points free from such factors. Noise and unstable heart rates, if not removed from the data pool, can affect the overall analysis of a patient's ECG record which can impact the overall results of QT studies or patient histories. Therefore, the present invention significantly improves the art by providing a method for which to provide optimum extractions of the ECG data.

Figure 2:
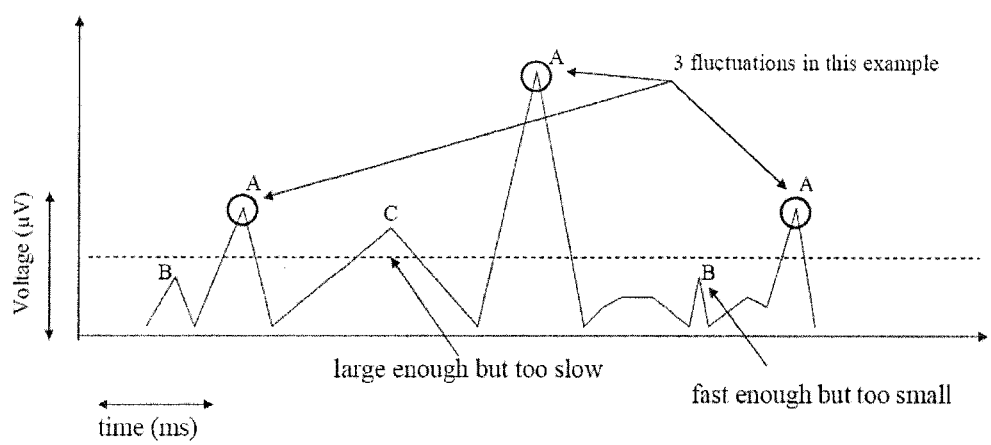
FIG. 2 is a graphical depiction exemplifying noise thresholds for use the present invention.

For the purposes herein noise threshold is defined as the sum of signal fluctuations larger than an amplitude threshold and shorter than a determined time limit. Referring to FIG. 2, an example of determining noise from useful data is shown. FIG. 2 exemplifies the noise threshold for use in the preferred embodiment of the present invention. In FIG. 2, the dotted line represents the amp threshold, meaning that any electrical activity above the threshold would qualify as noise. In the instant case, the threshold is 5 microvolts ($\mu V$). The second aspect of the noise threshold is a time component. With respect to ECG data, any electrical activity that is faster than a determined time period may be attributable to some other source than the electrical activity in the heart, or even if electrical data gathered from the heart, is not necessarily information that should be evaluated in analyzing the recorded ECG signals for one reason or another. In this particular instance, 20 milliseconds (ms) and under is determined to be the appropriate time period.

In the present embodiment, noise assessment is accomplished by analyzing the average count of signal fluctuations that are fast-enough (i.e. shorter than the time threshold) and large-enough (i.e. larger than the amplitude threshold). Other noise detection methods could be applied without changing the conceptual background of the invention (i.e. selection of lowest noise segment for extraction). Alternative method of noise assessment, such as usage of high-frequency filters applied to the ECG signal could be also implemented without changing the spirit of the invention. For example, with a high-pass fitter the time threshold would be replaced by the so-called "cut-off frequency" of the filter, and the amplitude threshold would remain the same.

Now referring again to FIG. 2, the amplitude noise threshold is fixed to 5 $\mu V$ and the time noise threshold is fixed to 20 ms. Accordingly, in reviewing FIG. 2, there are three fluctuations of data, designated as A in FIG. 2, that will be included in the noise count since both thresholds are met; the fluctuations A are large-enough and fast-enough. Of note, a time threshold of 20 ms would correspond to a frequency of 50 Hz, and thus, referring again to FIG. 2, the noise assessment consists of counting the signal content above 50 Hz with an amplitude of at least 5 $\mu V$. In two instances there appear to be fluctuations that are fast-enough, designated as B in FIG. 2, however, these instances are not large-enough to meet the amp threshold of 5 $\mu V$. Further, there is one fluctuation, designated as C in FIG. 2, that meets the amp threshold of 5 $\mu V$, but lasts for a time period longer than the fixed time noise threshold of 20 ms. Therefore, in reviewing FIG. 2 the three fluctuations A would be included in the count for noise specification, as defined, whereas the B and C fluctuations would not.

Further, unstable heart rates can also cause problems within the data pool, thus it is important to set parameters so that only segments with a stable heart rate on an ECG are taken, thereby eliminating other environmental factors from the data pool or record history.

Figure 3:
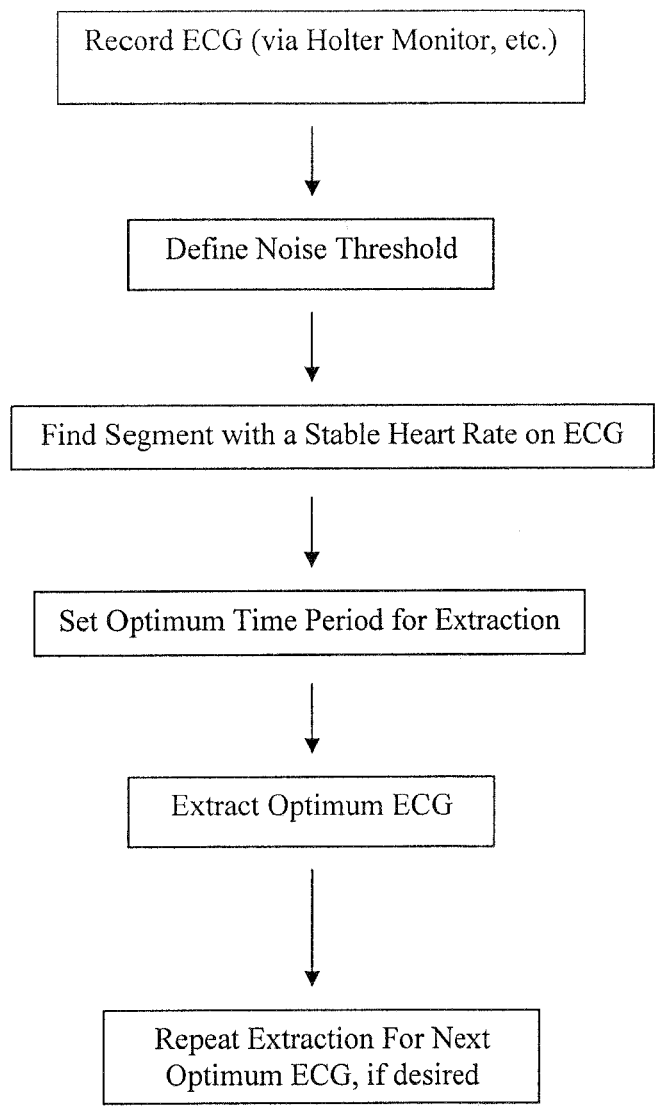
FIG. 3 is a flow chart depicting the method of the present invention.

The method of the present invention is for a ECG extraction system. Referring to FIG. 3, there is a flow chart of the method for the present invention. First, the ECG readings must be taken from a patient through some continuous monitoring system, possibly through a Holter monitor. Once the ECG data is established, the thresholds are provided to define noise within the ECG data by setting both time and amp thresholds above or below which is desired for optimum ECG readings. Once the thresholds are set for determining noise, the next step is to determine optimum time period around each programmed timepoint in which to take readings. At each programmed timepoint, the best ECG to be extracted are finally determined selecting the best candidates (i.e. the lowest noise and most stable preceding heart rate). The extraction step may be repeated as necessary to collect the second best and so on ECG data points. It should also be known that the steps of recording, defining noise, and finding segments of stable heart rates may be done in different orders, so long as they are all completed prior to extraction.

As mentioned previously, one problem existing in the field is the ability to extract ECG data that accounts for hysteresis heart rates either due to medication or activity in the patient without having to review the data manually. Therefore, another step in the method sets the timepoints for data collection/extraction. For instance, in clinical trials, one can predict, or actually know from blood-sample data, at what times drug reactivity or absorption should occur and can request the Holter device to capture ECG data during those time periods for later review. Other timepoints can be selected based on one or more factors, as well as setting general, regular intervals of data collection. In any event, the method should set a time period for capturing data based on the overall start and end point of the continuous reading or based on the factors such as levels of drug reactivity.

The method of the present invention may be embodied in a software program for extracting the optimum ECG data points from a continuous ECG record. The software program has one or more parametric features that may be selected by the user or can be run in a server client fashion by a separated process through an application program interface (API). The latter approach does not require the user interface, as the client process is in charge of setting all the parameters. These features let the user control the length of the extracted ECGs, the scalable output (sampling rate and amplitude resolution) the number of ECGs extracted at each timepoint, the duration of the optimum window and the timepoint rule of extraction (the fixed distance or from an external file). In its standalone (non server-client) implementation the program has one or more display menus to allow selection of the parametric values.

The invention a compares the instantaneous heart rate to the average heart rate computed over a preceding observation period; this comparison enables the program to extract the ECG readings with instantaneous heart rates that are closest to the average (stable) heart rate proximate the expected timepoint. As shown in the FIGS. 5, 6, and 7, a few milliseconds on either side of the expected timepoint can provide reliable signals when readings taken at the expected timepoint would have to be discarded if there is noise or an unstable heart rate.

Figure 4:
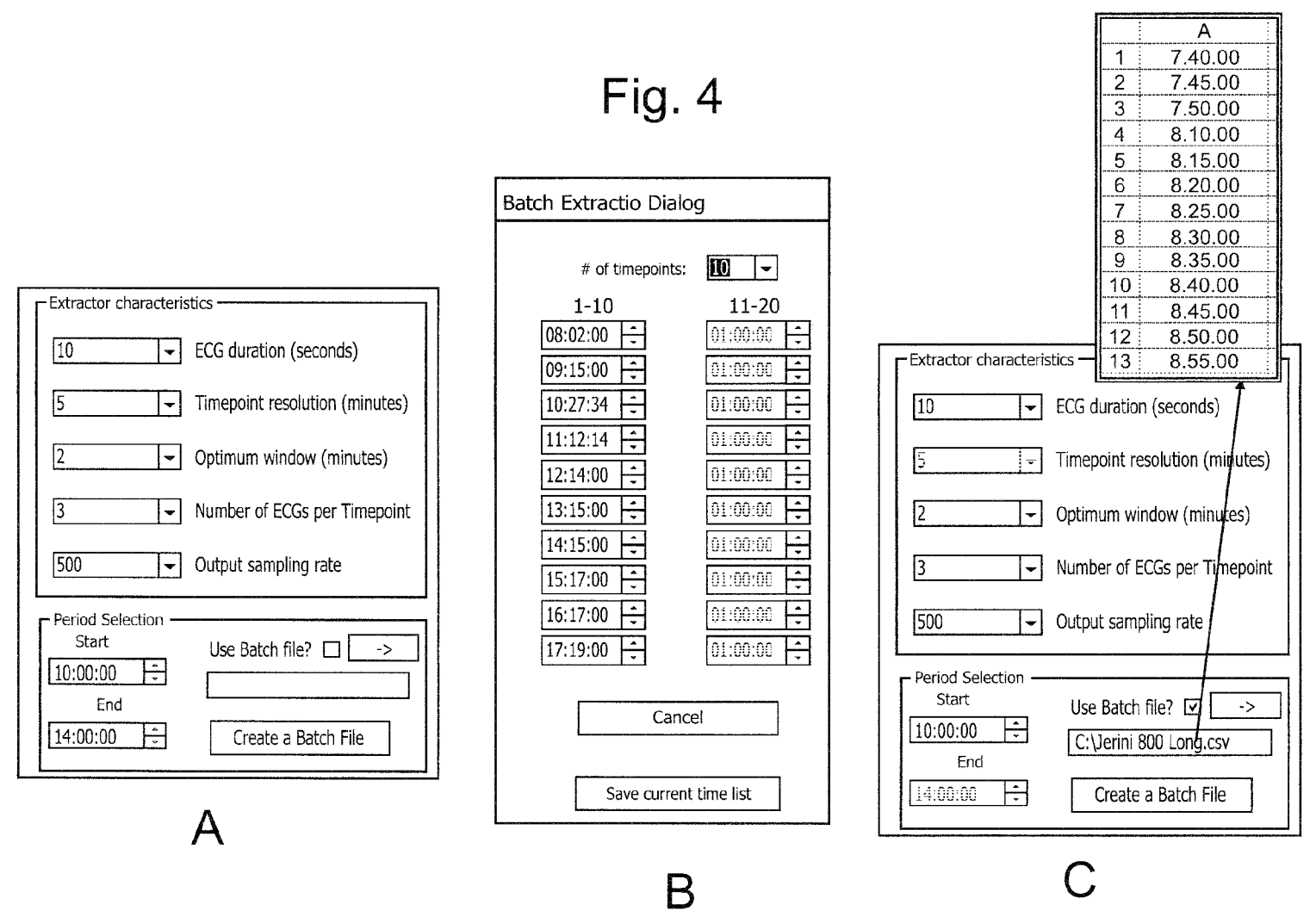

Now referring to FIG. 4, there is shown a display menu for the software extraction program showing a few of the parameters which may be set to enable optimum data extraction. The knowledge of creating such a software program is within the knowledge and understanding of one skilled in the art of computer or software programming. Specifically, the software program is executable either automatically or manually, and further used to extract data that is already recorded from monitoring devices by uploading files into the software program. The software program allows for setting the duration for ECG measurements, timepoint resolution, optimum timepoint window, number of ECGs per timepoint, and output sampling rate, as shown in A of FIG. 4. In other words, the features of a software embody the ability to: set the time of the extracted ECGs, make a scaleable output (i.e. sampling rate and amplitude resolution), set a number of ECGs to be extracted, and set the duration of the timepoint for an optimum window. Moreover, the software program allows for automatic data extraction by merely setting the number of timepoints and setting a start and end time for the timepoints, as shown in B of FIG. 4.

Such a software program could be implemented within a Holter device thereby assisting in recording or easily retrieving data from the Holter recordings. Further, the data can be extracted from external files that are imported into the system (i.e. imported full ECG records), and parameters to extract the data are similarly set as mentioned above, as shown in C of FIG. 4.

Figure 5:
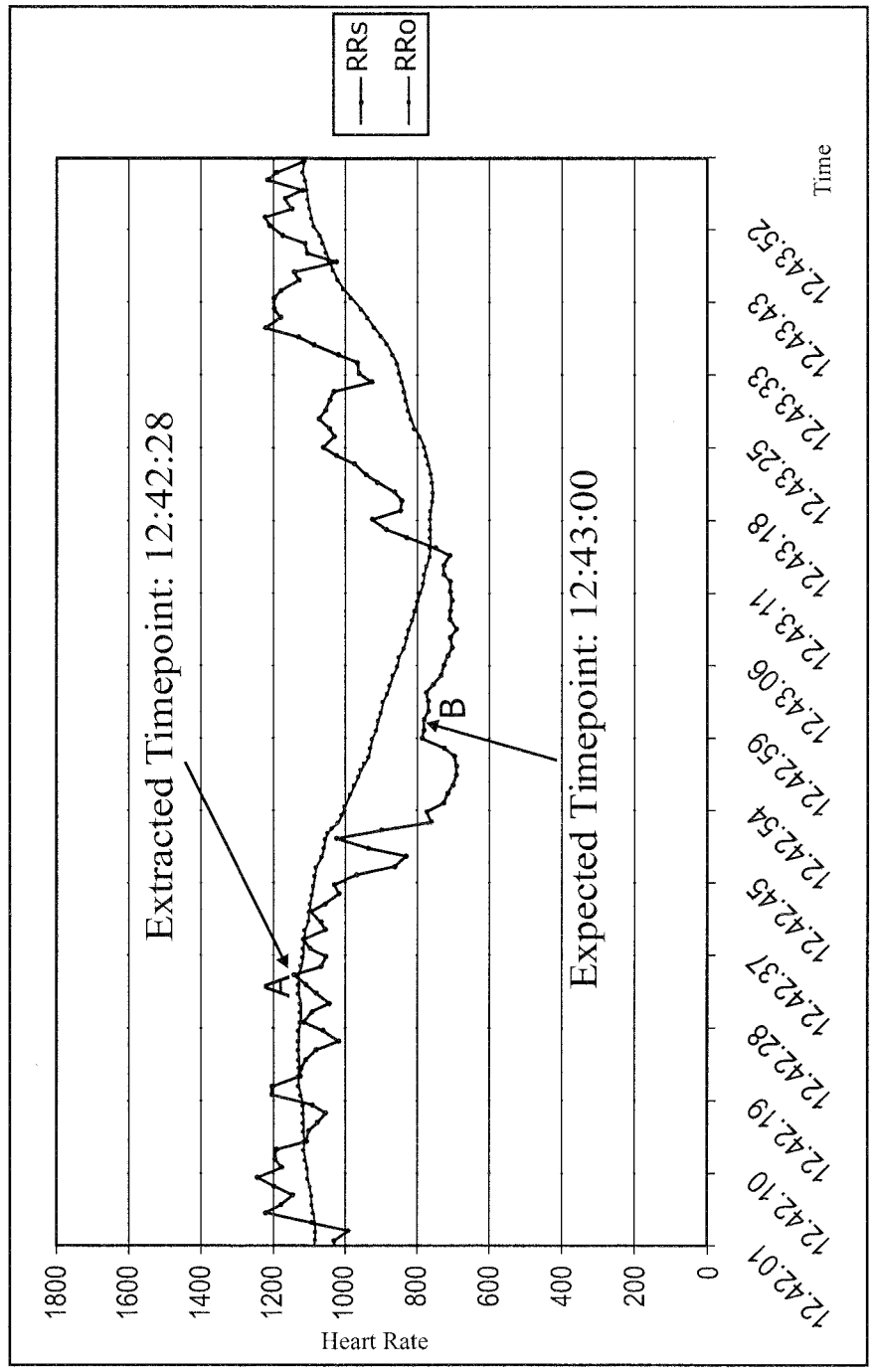
FIG. 5 is a graphical depiction time versus heart rate indicating an data point for expected extraction and a data point of optimum extraction using the method of the present invention. The $RR_s$ curve is the trend of the 10-second candidate extractions heart rate, whereas the $RR_o$ curve is the trend of the averaged rate computed over the minute preceding the candidate.

Referring now to FIG. 5, there is a graphic example of extracted data using the present invention. The graph depicts two RR intervals on a time scale at given points and refer to an example of a two-minute optimum period. The expected extraction time is 12:43 and thus the exploring window goes from 12:42 to 12:44. The $RR_S$ line is the instantaneous RR interval from each candidate extraction ($RR_S$ stands for $RR_{strip}$), and the $RR_O$ is the associated averaged RR interval from the minute preceding each candidate ($RR_O$ stand for $RR_{observationperiod}$). The RR interval is the time measurement from one QRS complex to the next QRS complex and it is used to determine patient heart rate (HR=1/RR) as well as heart rate variability. When the $RR_S$ and the $RR_O$ curves are close the candidate is preceded by stable heart rate. Conversely, when the $RR_S$ and the $RR_O$ curves are different they are preceded by either a heart rate acceleration or deceleration. The data is shown on the time in hour:minute:second scale on the x-axis versus the R-R interval on the y-axis.

There are two data points shown on the graph with one being the data point effectively chosen by the method of the present invention, shown as A in FIG. 5, and the other being the expected time point to extract, shown as B in FIG. 5. If the present invention were not implemented then the data extraction would have occurred at the expected timepoint B. In FIG. 5, the expected timepoint B to extract data was at timepoint 12:43:00. However, using the method of the present invention, setting an optimum time point window of about two minutes and parameters to determine noise as well as unstable heart rates, the optimum data point, A, was pulled, which is at 12:42:28.

As FIG. 5 shows, it appears the heart rate began to accelerate, which is demonstrated by the RR interval beginning to decrease, and therefore in determining a stable heart rate the expected timepoint, B, is discarded because it falls outside the parameters. By not extracting the expected timepoint, B, the data is more accurate and is not bias due to the acceleration in the heart rate possibly occurring through activity of the monitored individual. Accordingly, optimum data is extracted and can be analyzed by the clinician.

Figure 6A:
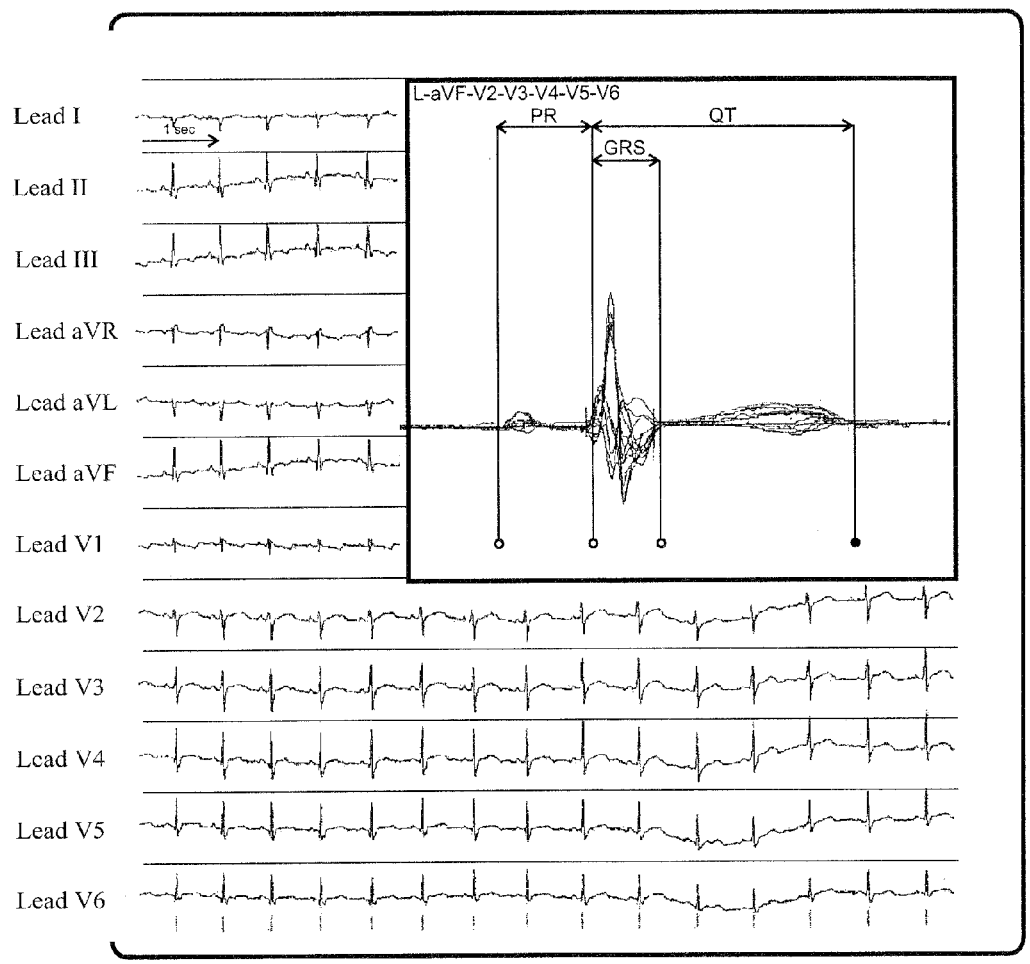
FIGS. 6A and 6B are views from two 12-lead ECG waveforms of superimposed representative beats displayed on a separate panel.
Figure 6B:
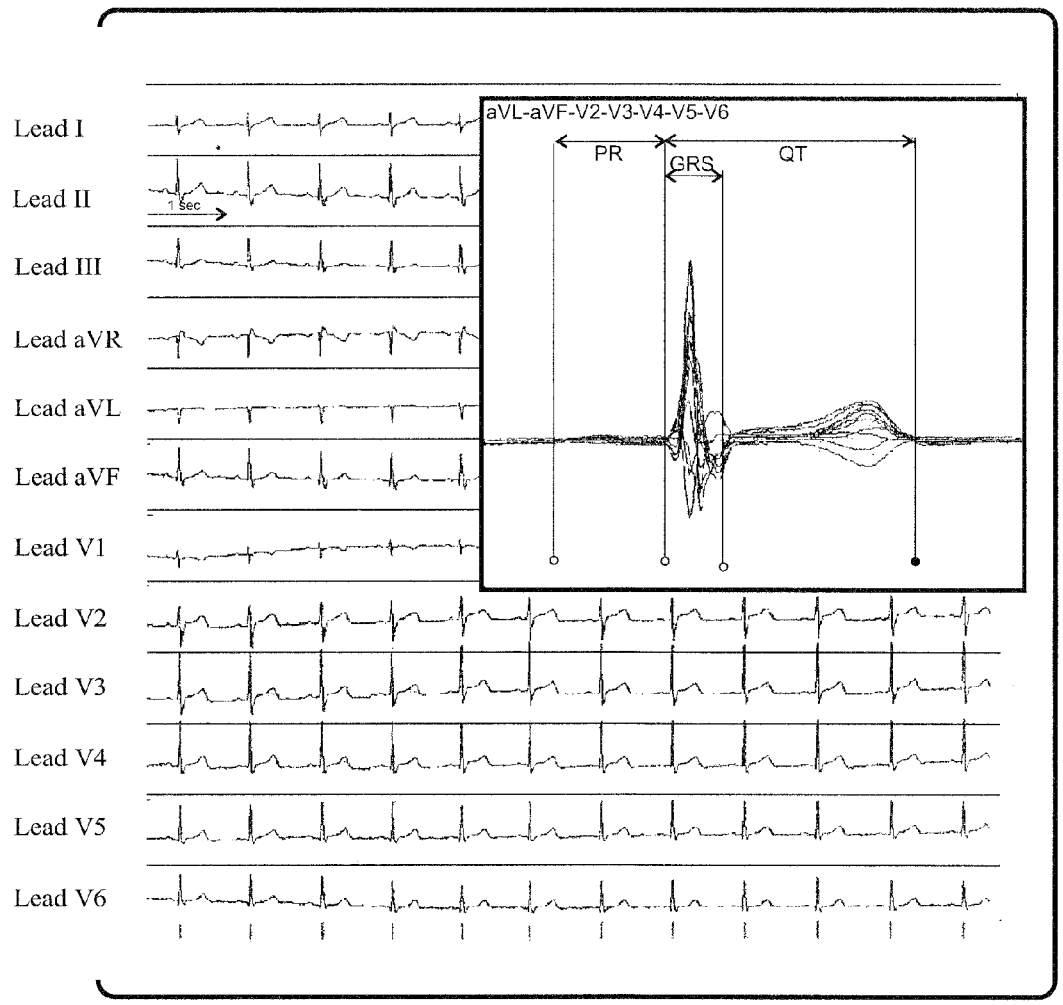

Referring to FIGS. 6A and 6B, there is a comparison of the ECG data from timepoints that are two minutes apart. FIG. 6A shows an ECG taken from a 12-lead device and taken at a timepoint of less than two minutes prior to timepoint of FIG. 6B. The ECG of FIG. 6A follows a sudden heart rate change, where as FIG. 6B is preceded by a stable heart rate. The measured parameters, which is discussed next, are quire different, despite the two ECGs being less than two minutes apart.

The ECG in FIG. 6A is from an expected timepoint whereas in FIG. 6B the ECG is one chosen by the method of the present invention through a software program. Looking at the data for the RR interval, the QT interval, as well as the QTcb and QTcf there is a significant difference in data within only two minutes. For instance the RR interval from FIG. 6A is 672 ms and the RR interval from FIG. 6B is 850 ms. The heart rate of FIG. 6A is faster than that of FIG. 6B, and, respectively, represent heart rates of 89 and 71 beats per minute. If an optimum window is about two minutes, selecting data from an arbitrary timepoint within the two-minute window could significantly impact data analysis, due to any number of factors such as noise or unstable heart rates. Therefore, with the method, a user can select and extract data from timepoints in an optimum window that are free from noise and other factors that could negatively affect data analysis.

Figure 7:
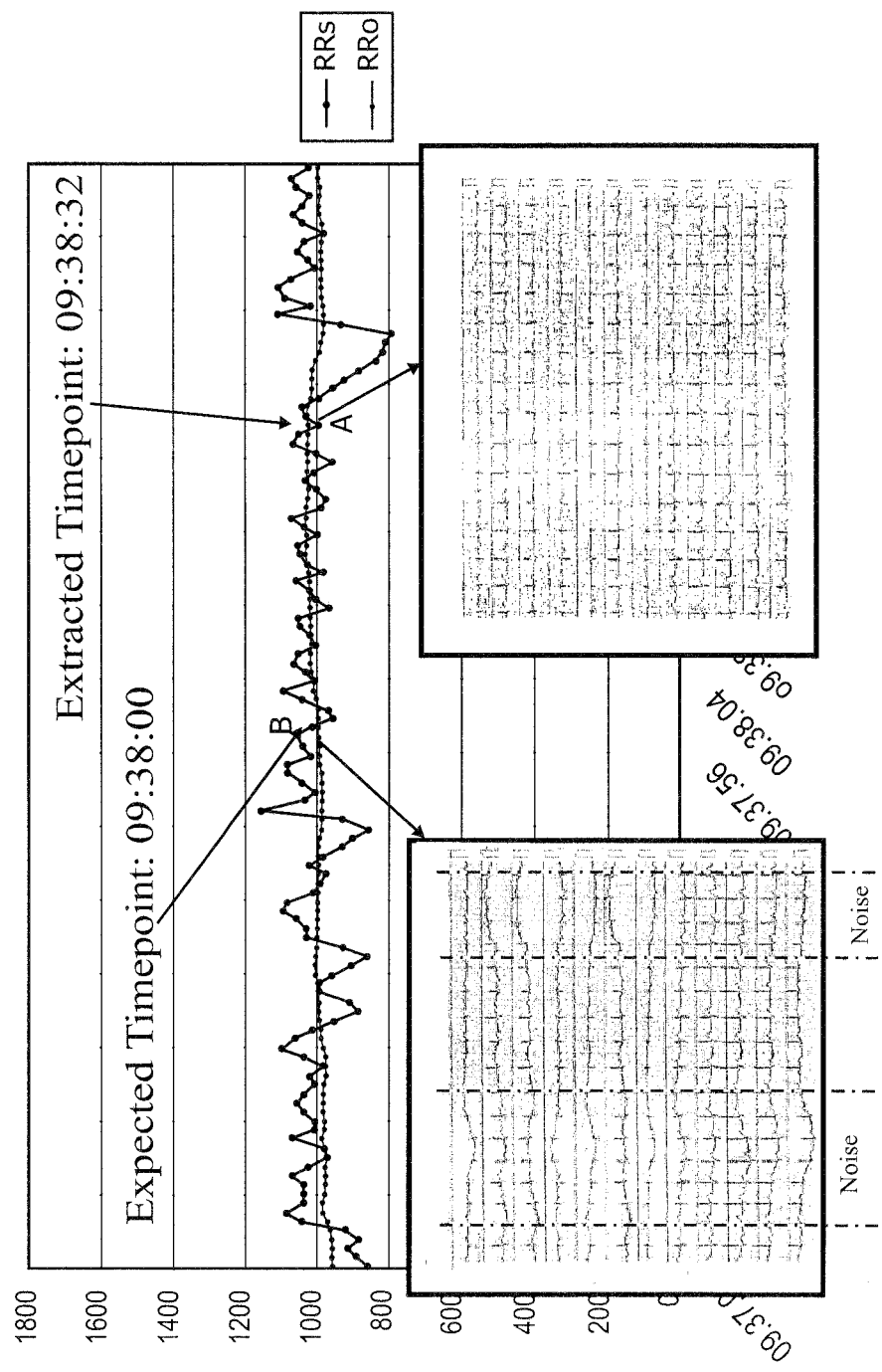
FIG. 7 is a graphical depiction of time versus heart rate showing an expected data point and an optimum data point with the respective 12-lead ECG waveforms for the respective data point exemplifying the benefits of the present invention.

Turning to FIG. 7, there is another depiction of data showing extraction of optimum data, A, and another point showing where expected data, B, could have been extracted. Further, there is an annotation showing the actual ECG depiction to exemplify the impact of the invention on the type of data extraction. In this example, the heart rate is rather stable throughout the two-minute optimum window, but the noise content in the ECG is not. Specifically, the heart rate is relatively stable throughout the whole exploring window. However, ECG in the middle has significant noise content, and the optimum extraction method selected a noise-free ECG 32 seconds later.

In looking at FIG. 7, the expected timepoint of data, B, is at 9:38:00, however, the extracted timepoint of data, A, was 9:38:32. The ECG data shows there is noise within the data at expected timepoint B. Specifically, the areas within the dotted lines, labeled as noise, show that there is some irregularity in the data. Such irregularities will affect the overall analysis either within a Phase I study for clinical drug testing or other uses, thereby leading to either inaccurate findings or diagnosis. Referring to the data of the extracted timepoint, A, the waveforms are regular, consistent, and free from noise or other potential forces that would affect data analysis. Accordingly, the present invention when used can extract ECG data from optimum window periods that are free from factors, such as noise or unstable heart rates, to provide accurate and consistent data for the clinicians use in determining patient conditions or assisting in determining efficacy and interactions of drugs on a patient and their heart, respectively.

Figure 8:
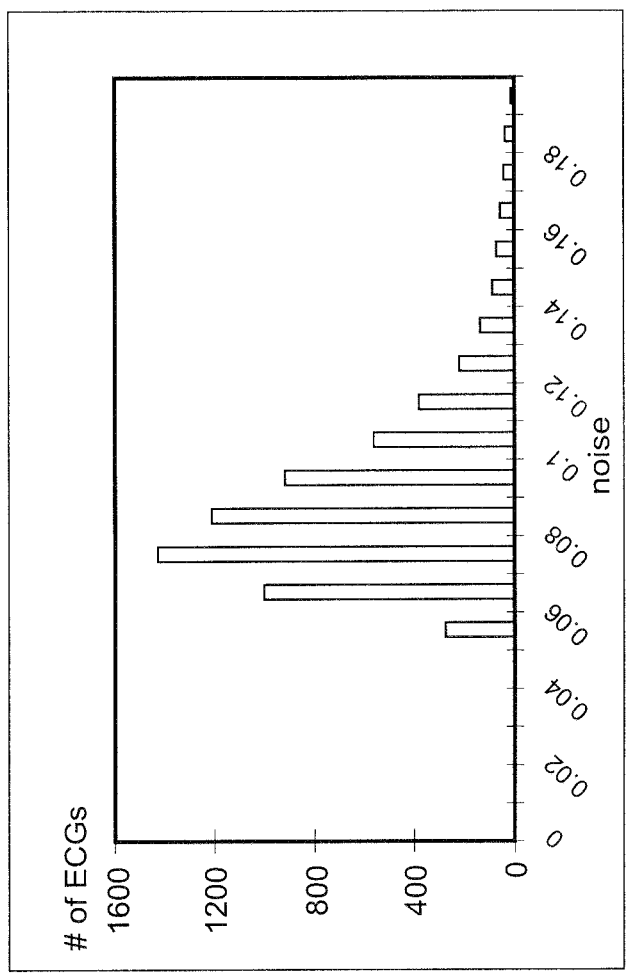
FIG. 8 is a summary histogram form 6536 extraction and give a categorical distribution of the noise content of the ECGs, thereby showing the advantage of the present invention in extracting data points with respect to noise reduction.
Figure 9:
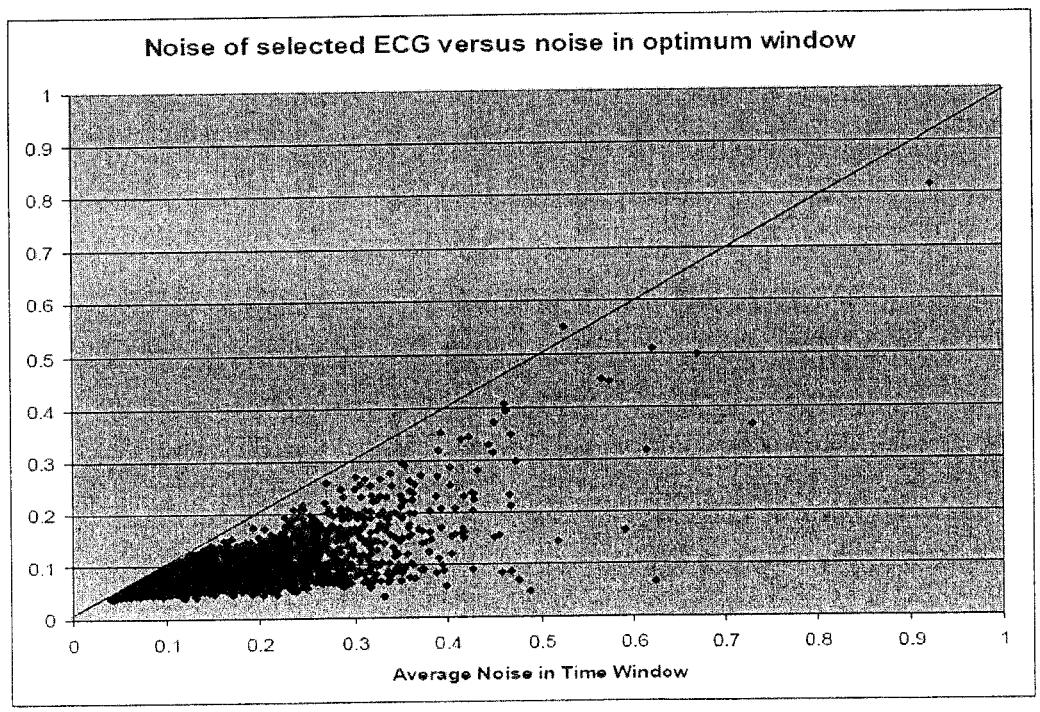
FIG. 9 is a graphical depictions showing the noise level in the extracted ECG versus the noise level in the extraction window, again, showing the advantage of the present invention in extracting data points with respect to noise reduction.

FIG. 8 is a histogram from 6536 extractions and give a categorical distribution of the noise content of the ECGs. FIG. 9 depicts the noise level of the noise level in the extraction window period versus extracted ECGs. As shown in FIG. 8, the level of noise found in all the ECGs collected, out of over 6500 ECGs, ranges between 0.06 and 0.12; fewer ECGs were found to have noise levels above 0.12. Moving to FIG. 9, the data shows noise levels in the optimum window period as a whole versus the noise level of the extracted ECGs. Again there is a cluster of ECGs showing noise levels below 0.3, and that the optimum ECGs are free from noise, which reiterates the impact of the present invention. Generally, FIG. 8 and FIG. 9 help to understand the usefulness of this method in providing categorical analysis on the noise content within a study, and indirectly become an accurate tool to assess the quality of both the device used to record the ECG and the core laboratories involved.

Figure 10:
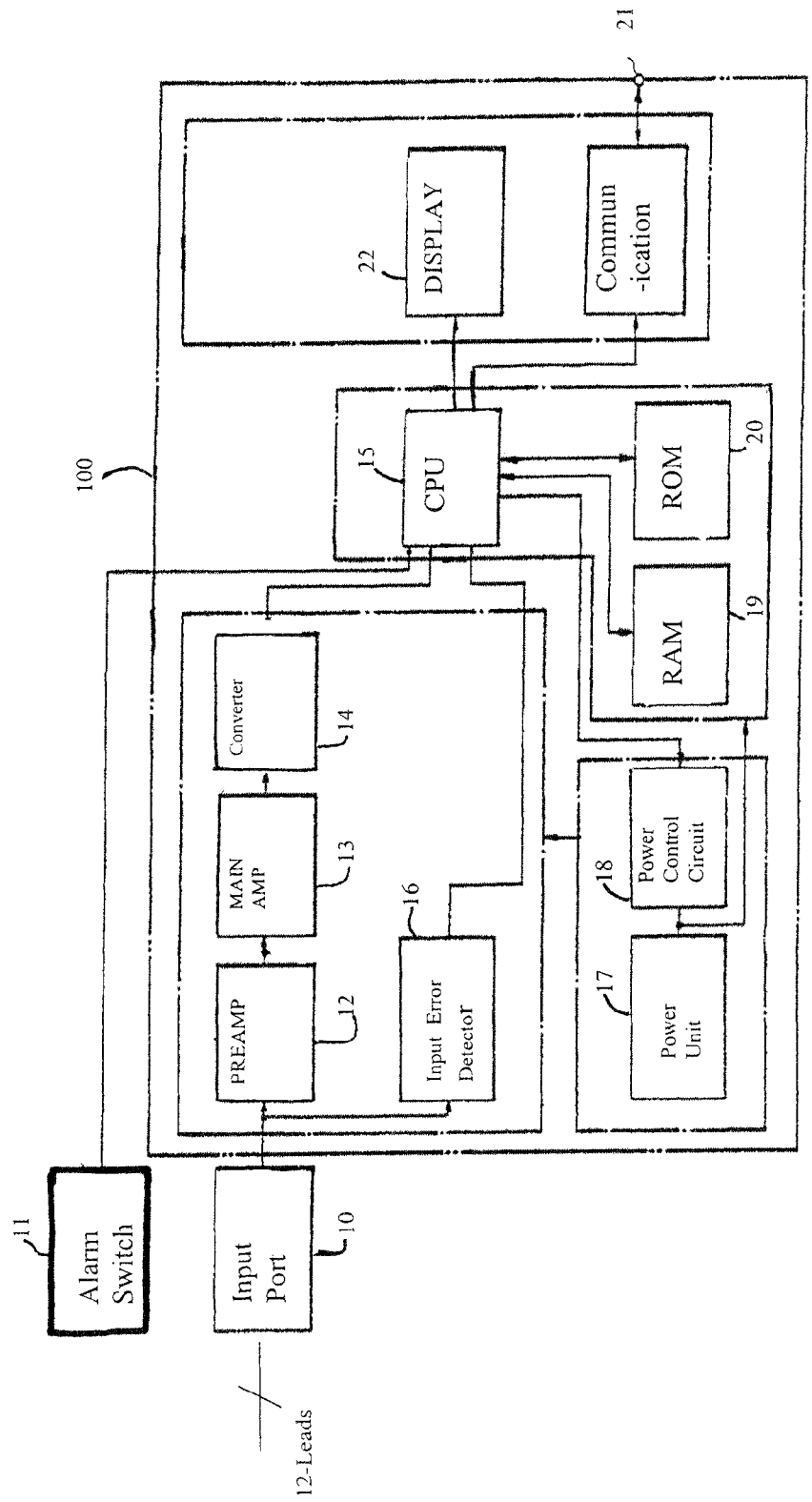
FIG. 10 is a block diagram showing an electrocardiograph monitor such as a Holter.

As shown in FIG. 10, an electrocardiograph monitor, such as a Holter, is generally made up of a body 100, an input port 10 for receiving ECG signals from 12 leads and from transmitting them to the electrocardiograph device. The electrocardiograph device may further contain an alarm switch 11, that a subject may operate in the event of palpitation, short breath, vertigo or similar cardiac symptom.

The electrocardiograph has a power unit 17 which is backed up, and a power source control circuit 18. The power unit 17 is a power source which uses a main battery and a back-up battery. When the voltage of the main battery is lowered beyond a predetermined voltage or when the main battery is to be replaced, the power supply source is automatically switched from the main battery to the back-up battery to maintain a predetermined output voltage at all times.

The preamplifier 12 amplifies faithfully AC components included in an ECG signal which is generated by the 12 leads. The 12 leads are affixed to a subject to produce ECG readings. Specifically, the preamplifier 12 is composed of two circuits, i.e., an operational amplifier and a DC cut-off filter which are interconnected in this order, although not shown in the figure. The operational amplifier has an input resistance as high as 1 megaohm or above so as to amplify the signal from the leads without being affected by the resistance of the living body, which is several kiloohms. Further, the operational amplifier serves to cancel in-phase noise introduced in the leads. The DC cut-off filter removes DC voltage components ascribable to the polarization of electrodes which are included in the leads.

The main amplifier 13 amplifies the output ECG signal of the preamplifier 12 to a level which is necessary for the AD converter 14 to convert the analog ECG signal to a digital signal. The converter 14 transforms the amplified analog ECG signal to a digital ECG signal in response to a conversion request which may be fed thereto from the CPU 15.

The input error detector 16 is responsive to various kinds of faults which may occur in the leads, i.e., separation between the skin and the electrodes, disconnection and other similar connection errors of the inputting section. On detecting such a fault, the input error detector 16 sends an error signal to the CPU 15.

The digital signal is processed by the CPU 15 and stored on the system RAM 19. System parameters are stored on the ROM 20, although may also be stored in RAM or on a storage device. A program for running the electrocardiograph apparatus is stored in the system memory, a storage device, RAM 19 or ROM 20. The inventive program provides optimum data points that are free from noise and accelerating or decelerating heart beats. As described above, the CPU 15 transmits the optimum data points to the display 22 or to an external device through the communication port 21. The display is capable of displaying charts or data as described above. Additionally, the communication port 21 allows for modification of the software programs loaded onto the electrocardiograph device.

While the invention has been described with reference to particular embodiments, it will be understood by those skilled in the art that various changes may be made and equivalents may be substituted for elements thereof without departing from the scope of the invention. In addition, many modifications may be made to adapt a particular situation or material to the teachings of the invention without departing from the scope of the invention.

Therefore, it is intended that the invention not be limited to the particular embodiments disclosed as the best mode contemplated for carrying out this invention, but that the invention will include all embodiments falling within the scope and spirit of the appended claims.

The invention claimed is:

1. A method for operating an electrocardiography (ECG) machine having a CPU, a memory, a display, and a software program in said memory for operating said ECG machine to identify and display low hysteresis optimum electrocardiography (ECG) heart rates by said electrocardiograph machine comprising the steps of:
   providing said electrocardiograph (ECG) machine to receive and record electrocardiograph signals from a patient who is continuously monitored by said ECG machine for one or more transient conditions of the electrical activity of the heart for an extended period of time;
   operating the ECG machine to record ECG signals generated by the patient's heart, said ECG signals occurring over an extended period of time and including at least one window of time, said window of time including a expected extraction time for an instantaneous and stable heart rate processing the ECG signals to calculate the heart rate for heart beats that occur during the window and to determine the average heart rate for an observation period preceding each heart beat during the window; and
   displaying a stable heart rate occurring during said window wherein said displayed stable heart rate is one of the heart rates in the windows that is closest in magnitude to its corresponding average heart rate; and wherein said displayed stable heart rate indicates a low hysteresis optimum electrocardiography (ECG) heart rate.

2. The method of claim 1 wherein one can predict, or actually know from blood-sample data at what times drug reactivity or absorption should occur and the predetermined time points correspond to one of the group comprising: (a) a predicted or actually known from blood-sample data showing there is a heightened level of drug interaction with or drug absorption by the patient; (b) a predicted or actually known blood-sample data showing there is a minimal level of drug interaction with or drug absorption by the patient; (c) a predicted or actually known blood sample data showing there is a predetermined level of drug interaction with or drug absorption by the patient; and (d) any combination thereof.

3. The method of claim 1 wherein the ECG signals are recorded by a portable monitor having continuous or extended recording capabilities.

4. The method of claim 1 wherein the window is a first predetermined time and the observation period is a second predetermined time prior to each heart beat.

5. The method of claim 4 wherein the window is two minutes and the observation period is one minute prior to each heart beat.

6. The method of claim 1 wherein the average heart rate is the running average of the heat beats occurring during the observation period preceding each heart beat.

7. A method for operating a machine with a central processing unit (CPU), a memory, a display, and a software program for operating said machine to identify and display low hysteresis electrocardiography (ECG) heart rates recorded by an ECG machine coupled to a patient for an extended period of time, comprising the steps of:
   said machine providing at least one window of time, said window of time including a expected extraction time for an instantaneous and low hysteresis heart rate, said expected extraction time corresponding to a predetermined time point when drug reactivity or absorption should occur;
   said machine recording in said memory said ECG signals including ECG signals inside and outside of said window;
   said machine processing the ECG signals to determine instantaneous heart rates for heart beats in said window and average heart rates for heart beats occurring during observation periods preceding each heart beat and storing said heart rates;
   said machine processing the ECG signals to compare each instantaneous heart rate during the window to the average heart rate of the heart beats during the observation period preceding each heart beat; and said machine displaying an instantaneous heart rate closest to the average heart rate during the corresponding preceding observation period.

8. The method of claim 7 wherein the predetermined time points correspond to one of the group comprising: (a) where from a predicted or actually known from blood-sample data there is a heightened level of drug interaction with or drug absorption by the patient; (b) where from a predicted or actually known from blood-sample data there is a minimal level of drug interaction with or drug absorption by the patient; (c) where from a predicted or actually known from blood-sample data there is a predetermined level of drug interaction with or drug absorption by the patient; and (d) any combination thereof; and wherein said displayed stable heart rate indicates a low hysteresis optimum electrocardiography (ECG) heart rate.

9. The method of claim 7 wherein the window is a first predetermined time and the observation period is a second predetermined time prior to each heart beat.

10. The method of claim 9 wherein the window is two minutes and the observation period is one minute prior to each heart beat.

11. The method of claim 7 wherein the average heart rate is the running average of the heat beats occurring during the observation period preceding each heart beat.

12. A method for operating a machine with a central processing unit (CPU), a memory, a display, and a software program for operating said machine to identify and display a stable, low hysteresis electrocardiography (ECG) heart rates recorded by an ECG machine coupled to a patient, comprising the steps of:

storing ECG data recorded over an extended duration of time;

setting at least one expected ECG data extraction time during the extended duration of time;

providing a window of time beginning before the expected extraction time and terminating after the expected extraction time;

calculating an instantaneous heart rate for heart beats occurring during the window;

calculating an average heart rate for heart beats occurring prior to each heart beat in said window;

at the expected ECG data extraction time, comparing the average heart rate during a preceding observation period to the instantaneous heart rate; and extracting an instantaneous heart rate within the window that is closest in magnitude to the average heart rate over a corresponding preceding observation period;

displaying said extracted instantaneous heart rate, wherein said displayed instantaneous heart rate indicates a stable, low hysteresis electrocardiography (ECG) heart rate recorded by said ECG machine.

13. The method of claim 12 wherein the window is a first predetermined time and the observation period is a second predetermined time prior to each heart beat.

14. The method of claim 13 wherein the window is two minutes and the observation period is one minute prior to each heart beat.

15. The method of claim 12 wherein the average heart rate is the running average of the heat beats occurring during the observation period preceding each heart beat.

* * * * *